Sept. 18, 1973 R. H. McCOLLEY Plant Pat. 3,399
DISTINCT VARIETY OF AGLAONEMA PLANT
Filed April 10, 1972
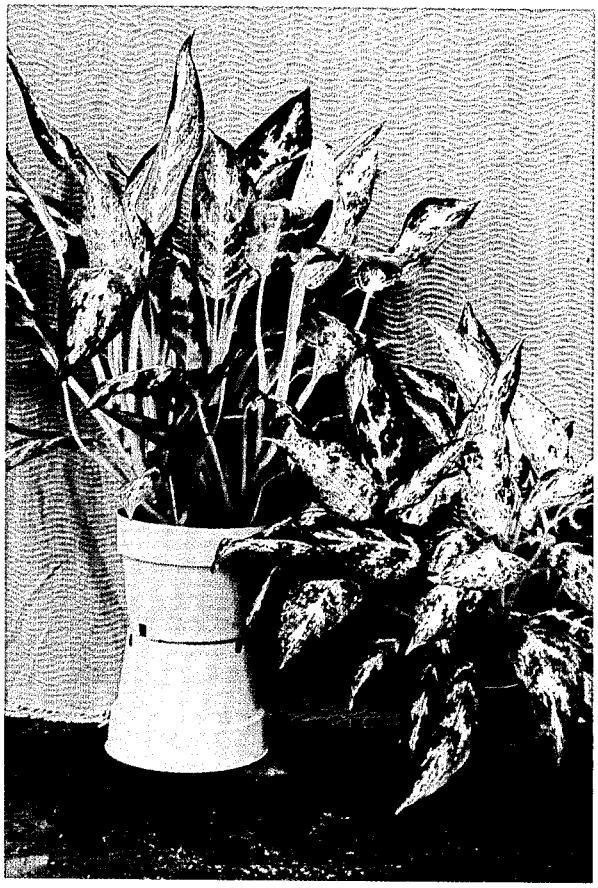

United States Patent Office

Plant Pat. 3,399
Patented Sept. 18, 1973

3,399

DISTINCT VARIETY OF AGLAONEMA PLANT

Robert H. McColley, P.O. Box 17126,
Orlando, Fla. 32810

Filed Apr. 10, 1972, Ser. No. 242,849
Int. Cl. A01h *5/00*
U.S. Cl. Plt.—88 1 Claim

ABSTRACT OF THE DISCLOSURE

The disclosure herein is of an Aglaonema plant, having the characteristic of producing a large proportion of white in the leaves, petioles and stems in relation to the green of the leaves, the green being distinctive and in view of the predominance of white providing a completely different impression with the white splotched throughout the leaves and many stems being entirely white.

DESCRIPTION OF THE INVENTION

My present new and distinct variety of Aglaonema plant was the result of a sport in production quantities of *Aglaonema pseudo-bracteatum* production in greenhouses in Orlando, Fla.

My new variety has been asexually reproduced repeatedly and has been found to retain its distinctive characteristics with very minor reversion to the species *A. pseudo bracteatum.*

While my instant variety is similar in many respects to the parent *A. pseudo bracteatum* which is an industry standard, my new variety displays what I believe to be two to three times as much white in the leaf, petiole and stem. There is thus in the overall impression an Aglaonema available with far more color than has ever been available before, the color being a combination of the green and white as should be readily understood.

My new vareity has a large number of recognizable visual characteristics including an ovate leaf with obtuse leaf base and acuminate leaf tip.

The leaves further have pinnate veination and are alternately placed on the stem. The leaf surfaces may be smooth to undulate on the surfaces, with shunken midrib and veins.

The white stems and petioles are occasionally splotched with green and further distinctive means for recognition.

The petioles may be semi-erect to erect, and equal to or slightly less in length than the leaf itself.

The leaf in most cases, has an irregular margin of green therearound with 25 to 50% of the leaf having white splotches irregularly scattered on the surface thereof.

The detailed specifications set forth hereinafter are based on observations made in a greenhouse in Orlando, Fla. The specifications may vary in environmental variations, but where the environmental conditions remain the same, including temperature, humidity, daylight length, light intensity and available nutrients, the plants will reproduce true to form.

The accompanying drawing forming a part thereof, shows a typical plant of my new variety, the color being as nearly true as possible with color illustrations of this type.

The color references are made to the Nickerson Color

Fan published by Munsell Color Company, observations being recorded by daylight illumination under vinyl of not more than 30% shade. Comparison has been made and results in distinguishing from the industry standard *Aglaonema pseudo bracteatum.*

Certain of the particular characteristics distinguishing my new variety from the industry standard *Aglaonema pseudo bracteatum* is the fact that the petioles in virtually all instances and the stems themselves are white as compared with the speckled white of the industry standard mentioned, and this together with the very large percentage of white over the leaf surface, estimated at 50% as compared with 10% in the Pseudo Bracteatum, is a further means for distinguishing the same from its parent.

(I) Form characteristics:

| | |
|---|---|
| (1) Leaf itself | Ovate. |
| (2) Leaf tip | Acuminate. |
| (3) Leaf base | Obtuse. |
| (4) Leaf displacement | Smooth to undulate. |
| (5) Leaf margin | Entire. |
| (6) Leaf veination | Sunken midrib and veins. |
| (7) Leaf attachment | Stalked. |
| (8) Leaf arrangement | Alternate; horizontal to erect. |
| (9) Petiole | Medium length, erect. |
| (10) Stem | Sturdy, very short internodes. |
| (11) Overall appearance | Medium density. |

(II) Size characteristics of typical commercial size:

| | Inches |
|---|---|
| (1) Leaf itself: | |
| (a) Width—widest point | 2–3½ |
| (b) Width—1" from tip | ½ |
| (c) Length | 6–10 |
| (d) Thickness | .015–.020 |
| (2) Petiole length | 5–9 |
| (3) Petiole diameter (middle) | ⅛–3/16 |
| (4) Internode spacing | ¼–⅝ |
| (5) Stem diameter | ⅜–⅝ |

(III) Color characteristics:

| | |
|---|---|
| (1) Leaf: | |
| (a) Color pattern | Green splotched to 50% white. |
| (b) Color numbers | 7.5GY 4/4 variations of 2.5GY 8/9 to 2.5GY 7/10. |
| (2) Midrib | Varies; all 3 colors. |
| (3) Veins | Same as midrib. |
| (4) Petiole | White. |
| (5) Stem | Do. |

I claim:

1. A new and distinct variety of Aglaonema plant substantially as herein disclosed, characterized as to novelty by the superior growth and keeping qualities, as well as large proportion of white in the leaves, petioles and stems in relation to the moderate olive green to brilliant yellow green extending throughout the other portions of the leaves, petioles and stems.

No references cited.

ROBERT E. BAGWILL, Primary Examiner